(12) United States Patent
Hierro Pilas

(10) Patent No.: US 11,311,621 B2
(45) Date of Patent: Apr. 26, 2022

(54) ORGANOSILICON COMPOUND MICROPARTICLES AND PROCESS FOR THEIR PREPARATION

(71) Applicant: SILICIUM ESPAÑA LABORATORIOS, S.L., Vila-Seca (ES)

(72) Inventor: Joan Carles Hierro Pilas, Vila-Seca (ES)

(73) Assignee: SILICIUM LABORATORIES, LLC, Miami, FL (US)

( * ) Notice: Subject to any disclaimer, the term of this patent is extended or adjusted under 35 U.S.C. 154(b) by 0 days.

(21) Appl. No.: 16/978,173

(22) PCT Filed: Mar. 5, 2019

(86) PCT No.: PCT/EP2019/055401
§ 371 (c)(1),
(2) Date: Sep. 3, 2020

(87) PCT Pub. No.: WO2019/170646
PCT Pub. Date: Sep. 12, 2019

(65) Prior Publication Data
US 2021/0038727 A1 Feb. 11, 2021

(30) Foreign Application Priority Data
Mar. 6, 2018 (EP) .................... 18382138

(51) Int. Cl.
| | |
|---|---|
| *A61K 47/36* | (2006.01) |
| *A61K 8/58* | (2006.01) |
| *A61K 8/73* | (2006.01) |
| *A61K 8/02* | (2006.01) |
| *A61K 31/695* | (2006.01) |
| *A23L 33/10* | (2016.01) |
| *A23L 29/00* | (2016.01) |
| *A23L 29/25* | (2016.01) |
| *A61K 9/00* | (2006.01) |
| *A61K 9/16* | (2006.01) |
| *A61Q 19/00* | (2006.01) |

(52) U.S. Cl.
CPC .............. *A61K 47/36* (2013.01); *A23L 29/03* (2016.08); *A23L 29/25* (2016.08); *A23L 33/10* (2016.08); *A61K 8/0241* (2013.01); *A61K 8/585* (2013.01); *A61K 8/73* (2013.01); *A61K 9/0095* (2013.01); *A61K 9/16* (2013.01); *A61K 9/1688* (2013.01); *A61K 31/695* (2013.01); *A61Q 19/00* (2013.01); *A23V 2002/00* (2013.01); *A61K 2800/10* (2013.01); *A61K 2800/412* (2013.01)

(58) Field of Classification Search
CPC ..... A61K 9/0095; A61K 47/36; A61K 31/695
See application file for complete search history.

(56) References Cited

U.S. PATENT DOCUMENTS

| | | | |
|---|---|---|---|
| 2007/0141137 A1* | 6/2007 | Nagahara | A61K 47/42 424/451 |
| 2007/0205303 A1* | 9/2007 | Nayak | B01D 1/18 239/222.11 |
| 2018/0303761 A1* | 10/2018 | Xu | A61K 47/42 |

FOREIGN PATENT DOCUMENTS

| | | |
|---|---|---|
| EP | 0242855 A2 | 10/1987 |
| WO | WO 2011/039336 A1 | 4/2011 |

OTHER PUBLICATIONS

Araujo, An Bras Dermatol, 2016, 91(3), 331-335.*
International Search Report and Written Opinion dated Apr. 25, 2019 for International Patent Application No. PCT/EP2019/055401, 12 pages.

* cited by examiner

*Primary Examiner* — Kyle A Purdy
(74) *Attorney, Agent, or Firm* — Squire Patton Boggs (US) LLP

(57) ABSTRACT

Organosilicon compound microparticles and process for their preparation It is provided a combination of an organosilicon compound and arabic gum in the form of microparticles, wherein the organo silicon has the formula (I): wherein $R^1$ and $R^2$ are independently selected from hydrogen and a $(C_1C_4)$alkyl group; $R^3$ is hydroxyl; and $R^4$ is hydroxyl or a $(C_1C_4)$ alkyl group; the arabic gum is forming a polymeric matrix having interspaces, and the organosilicon compound is distributed in the interspaces of the polymeric matrix. It is also provided a process for its preparation and a composition comprising the mentioned combination.

20 Claims, 4 Drawing Sheets

ORGANOSILICON COMPOUND MICROPARTICLES AND PROCESS FOR THEIR PREPARATION

CROSS-REFERENCE TO RELATED APPLICATIONS

This application is a 35 U.S.C. § 371 application of International Application No. PCT/EP2019/055401, filed on Mar. 5, 2019, which claims the benefit of European Patent Application EP18382138.8 filed on Mar. 6, 2018, the entireties of which are hereby incorporated by reference.

TECHNICAL FIELD

The present invention relates to compounds containing biologically active silicon, which are under solid form, to processes for the preparation thereof, and to their use as a dietary supplement.

BACKGROUND ART

Biologically active silicon compounds are organosilicon compounds capable of being absorbed by the organism. Particularly, they have various silanol Si—OH bonds. Silanols are characterized by having a form of silicon assimilable by the body, due to their property of existing in aqueous solution in the form of soluble oligomers of low molecular weight. Biologically active silicon compounds are usually available as diluted solutions, since they tend to polymerize when they are too concentrated.

As an example, monomethylsilanetriol (MMST; CAS No: 2445-53-6), has the following chemical structure:

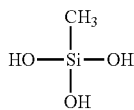

Biologically active silicon compounds in aqueous solutions tend to polymerize when they are too concentrated. Thus, the solubility of MMST in water at 21° C. without irreversible polymerization after 2 months is of up to 21 mM (equal to 588 mg Si/L). It is further indicated that, like all monomeric silicon species, MMST suffers spontaneous self-association in a concentration-dependent manner. This limits the solubility of the compound since solid phase polymers will be formed at high concentrations. MMST is commercially available as a 4.1 mM (115 mg Si/L) aqueous solution having a pH of 6.6, or in the form of a solid salt thereof.

There is still the need of finding stable organosilicon compounds under solid form.

SUMMARY OF INVENTION

The inventors have found that certain organosilicon compounds can form particularly stable solid forms with arabic gum. Additionally, the solid form has a good homogeneity. The provision of the mentioned solid form provides a new tool to overcome the problems associated with the stability of organosilicon compounds, and thus it is considered a contribution to the art.

Thus, a first aspect of the invention refers to the provision of a combination of an organosilicon compound and arabic gum in the form of microparticles, wherein the organosilicon has the formula (I):

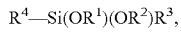

wherein $R^1$ and $R^2$ are independently selected from hydrogen and a $(C_1-C_4)$alkyl group; $R^3$ is hydroxyl; and $R^4$ is hydroxyl or a $(C_1-C_4)$alkyl group;

the aragic gum is forming a polymeric matrix having interspaces, and the organosilicon compound is distributed in the interspaces of the polymeric matrix.

Another aspect relates to a process for the preparation of the combination as defined above comprising:
a) preparing an aqueous solution of the organosilicon compound of formula (I) as defined above;
b) mixing the solution with a suitable amount of arabic gum in order to obtain an aqueous suspension; and
c) drying the suspension either by spray drying or by fluidized bed encapsulation in order to obtain a solid product.

Another aspect relates to a pharmaceutical or a cosmetic composition comprising the combination of an organosilicon compound and arabic gum in the form of microparticles as defined above, together with pharmaceutically or cosmetically acceptable excipients or carriers.

DETAILED DESCRIPTION OF THE INVENTION

Figure 1:
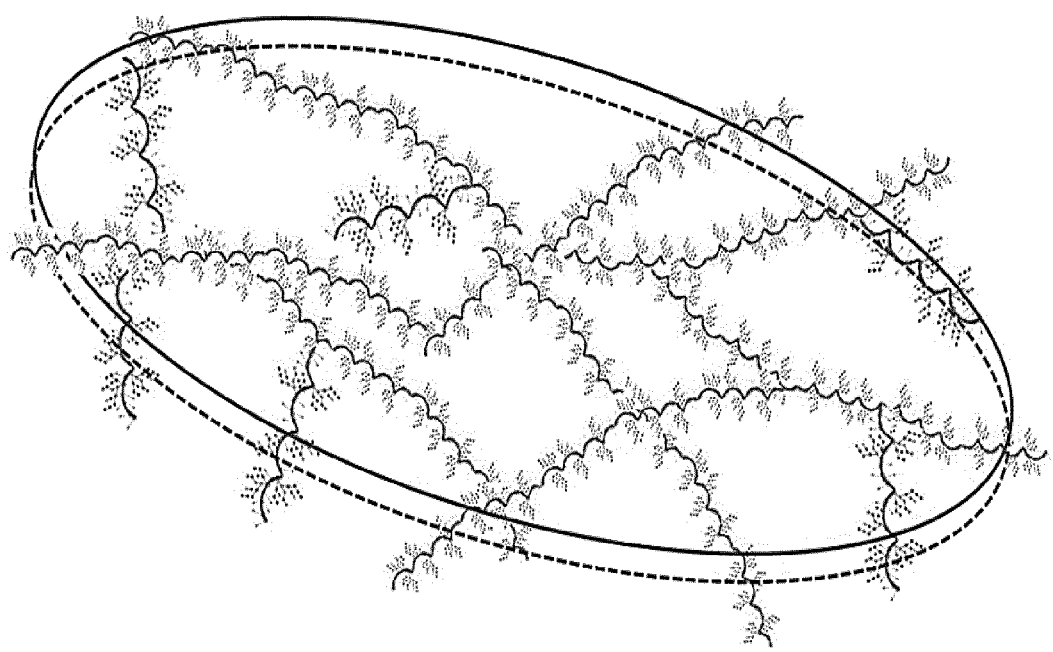
FIG. 1 shows an illustration symbolizing an example of the three-dimensional structure of arabic gum.
Figure 2:
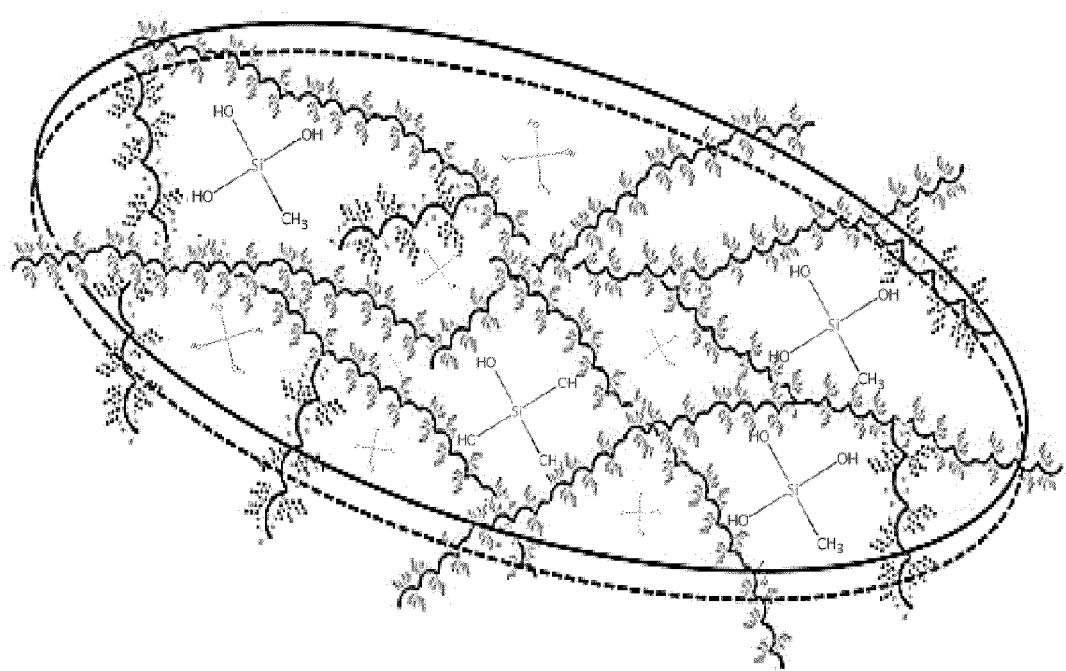
FIG. 2 shows an illustration symbolizing an example of a microparticle of the composition of the present disclosure wherein arabic gum is forming a three-dimensional structure wherein MMST is embedded.

The term "$(C_1-C_4)$ alkyl" refers to a saturated straight, or branched hydrocarbon chain that contains from 1 to 4 carbon atoms. Examples include, among others, the group methyl, ethyl, propyl, isopropyl, butyl, isobutyl, sec-butyl, and tert-butyl.

As used herein, the term "microparticle" refers to a solid matrix particle wherein the solid matrix is made of polymer chains forming a three-dimensional structure having interspaces among the chains wherein an active ingredient is embedded.

As used herein, the term "embedded" refers to an arrangement of the active ingredient, particularly the organosilicon compound as defined herein above and below, such that it is distributed in the interspaces formed by polymer chains forming a polymeric matrix. Particularly, in the combination of the organosilicon compound and arabic gum in the form of microparticles of the present invention, the organosilicon compound is homogeneously distributed in the interspaces of the polymeric matrix.

The terms "particle size" and "particle size distribution", as used herein, are in terms of diameter irrespective of the actual particle shape. The term "diameter", as used herein, means the equivalent sphere diameter, namely the diameter of a sphere having the same diffraction pattern, when measured by laser diffraction, as the particle. The diameter of nanoparticles as well as the particle size distribution can be measured by granulometry, Thus, a granular sample is worked through a series of sieves with decreasing hole sizes.

As a consequence, the different grains in the sample are separated according to their sizes.

The term "room temperature (RT)" refers to a temperature of the environment, without heating or cooling, and is generally comprised from 20° C. to 25° C.

All percentages used herein are by weight of the total composition, unless otherwise designated.

As used herein, the indefinite articles "a" and "an" are synonymous with "at least one" or "one or more." Unless indicated otherwise, definite articles used herein, such as "the," also include the plural of the noun.

Arabic gum or acacia gum (CAS No: 9000-01-5) is a biopolymer, a type of water soluble fiber, made of hardened sap taken from two species of the acacia tree: Acacia Senegal and Acacia Seyal. It is commercially available. Arabic gum is not digestible in the human small intestine and does not occur naturally in food. It is mainly used in the food industry as a stabilizer (E414). This gum has been evaluated and recognized as a food additive having prebiotic properties and a low glycemic index. In addition, it has been shown to be a material that favours the inhibition of the growth of microorganisms.

The molecular weight of the arabic gum is from 200 to 600 kDa, being a complex mixture of polysaccharides and glycoproteins, among which the following are recognized: branched galactane composed of a main chain of D-galactose units and side chains of D-glucuronic acid with terminal units of L-rhamnose or L-arabinose. The chemical structure of arabic gum also contains small amounts of nitrogenous material.

The polysaccharide fraction of arabic gum is a branched chain, with a molecular weight that can vary from 47,000 to 3,000,000 g/mol. The linear chain is composed of (1,3) β-D-galactopyranosyl units and branches to the sides of (1,6) β-D-galactopyranolsyl-4-O methyl glucuronic, which, in turn, are attached to smaller branches composed of L-rhamnose-D-glucuronic acid, D-galactose-(1,3) and L-arabinose and L-arabinose (1,3)-L-arabinose (1,3) L-arabinose. The nitrogenous material is of the protein type, corresponds to up to 10% of the total weight, and in particular in Senegalese and Seyal species it is around 2%. For this reason, arabic gum has been designated as a protein complex-arabinogalactan.

The protein fraction of arabic gum consists of 400 amino acid residues, with 18 different amino acids, of which 50% corresponds to hydroxyproline, serine and proline, and it is considered that the polysaccharide binding is most likely to occur through the hydroxyproline route bound to arabinose residues. Due to its structural characteristics, arabic gum has an amphiphilic character, which allows it to absorb on lipophilic surfaces, act as a protective colloid and, therefore, as a good film-forming agent; additionally, it presents low viscosity and Newtonian behavior at concentrations lower than 35%. Thus, the arabic gum is one of the most effective film forming materials for microencapsulation.

As mentioned above, the first aspect of the present disclosure relates to a combination in solid form consisting of an organosilicon compound as defined herein above and below and arabic gum.

In an embodiment of the combination in solid form, $R^4$ a $(C_1-C_4)$ alkyl group, particularly, methyl. For example, the organosilicon compound can be monomethylsilanetriol. In another embodiment, the organosilicon compound can be orthosilicic acid.

As mentioned above, the combination in solid form as defined above is in the form of microparticles.

As an example, microparticles can have a diameter from 10 to 250 μm, or from 20 to 150 μm. Particularly, microparticles have a narrow particle size distribution (geometric standard deviation). In order to determine the mentioned particle size and particle size distribution, a granular sample can be worked through a series of sieves with decreasing hole sizes, such as with a metallic sieve.

In another embodiment, optionally in combination with one or more features of the particular embodiments of the combination in solid form defined above, the organosilicon compound is in an amount from 1 to 10 wt %, or from 1 to 5 wt %, relative to the total weight of the composition.

In another embodiment, optionally in combination with one or more features of the particular embodiments of the combination in the form of microparticles as defined above, the combination in solid form as defined above is a dietary supplement.

The combination in the form of microparticles, according to the present disclosure can be prepared by:
 a) preparing an aqueous solution of the organosilicon compound of formula (I) as defined above;
 b) mixing the solution with a suitable amount of arabic gum in order to obtain an aqueous suspension; and
 c) drying the suspension by spray drying in order to obtain a solid product.

The aqueous solution of organosilicon compound can be obtained by dissolving in water a salt of the organosilicon compound, such as sodium or a potassium salt thereof, and adding an acid such as phosphoric acid to the aqueous solution so that the salt of the organosilicon compound is hydrolyzed and an aqueous solution of highly concentrated organosilicon compound is obtained. Once the hydrolysis reaction has been completed, gum arabic such as in the form of an aqueous suspension is added under stirring in order to get a homogeneous suspension.

In an example the organosilicon compound is MMST. In an example, the aqueous solution of MMST can be obtained from methyltriethoxysilane (MTES) by hydrolysis with a weak acid such as citric acid. The amount of salt of MMST in the aqueous suspension containing the mentioned compound and gum arabic will be such that the amount of MMST in the final combination in solid form, i.e. after removal of the water, will be from 1 to 10 wt %, particularly from 1 to 5 wt %, relative to the total amount of MMST and arabic gum.

As mentioned above, drying is carried out by spray drying. Particularly, the obtained suspension can be sprayed by an process of spray drying with drying tower, which allows rapid drying and avoids the polymerization of the organosilicon compound in the gum arabic, which is acting as a carrier. Thus, a solid product that can be kept for months is obtained, still without adding conservatives.

As an example, spray drying can be carried out in a spray dryer equipped with a nozzle of a diameter from 1 to 40 mm, or from 2 to 20, or from 5 to 10, particularly, at a rotational speed from 17000 to 19000 rpm, or from 17400 to 18600. More particularly, spray drying is carried out in a dryer with an inlet temperature from 150 to 230° C., or from 215 to 225° C., and an outlet temperature from 65 to 120° C., or from 95 to 115° C. Even more particularly, the particles when leaving showed a linear speed of 100 to 150 m/s.

Alternatively, the combination in the form of microparticles according to the present disclosure can also be prepared by fluidized bed encapsulation, such as in a Wurster chamber. In this process the microencapsulation is produced by suspending small particles of the organosilicon compound in a bed of air, while dispersing on them, in the form of fine rain, a water solution of gum arabic. The film is formed by evaporation of the water.

The combination in the form of microparticles obtainable by any one of the processes mentioned above also forms part of the invention.

Throughout the description and claims the word "comprise" and variations of the word, are not intended to exclude other technical features, additives, components, or steps. Furthermore, the word "comprise" encompasses the case of "consisting of". The following examples and drawings are provided by way of illustration, and they are not intended to be limiting of the present invention. Furthermore, the present invention covers all possible combinations of particular and preferred embodiments described herein.

EXAMPLES

General Procedure

Preparation of microparticles was carried out by the method of spray drying. First, suspensions were prepared by weighing and dispersing either gum arabic in distilled water by using a propeller agitator at 1700 rpm±300 and 29.52±1.92° C., for one hour. Then, MMST previously dissolved in water was added to the mentioned suspension, and stirring was continued for an additional period of 30 min. The viscosity and pH of the dispersion comprising MMST and gum arabic was measured by using a viscometer and an pH meter. Microparticles were obtained by drying the suspension in a spray dryer equipped with a 0.5 mm diameter nozzle. The rotational speed was controlled at 18000 rpm±600 and the particles when leaving showed a linear speed of 100 to 150 m/s. The inlet and outlet temperature of the dryer was maintained at 220±5 and 105±10° C., respectively. The feed speed of the sprinkler system was 3.3 L/min.

Arabic gum led to initial solutions with a pH of 4.3-4.6 Several experiments were carried out. Initially not clear solutions were obtained before spray drying. The initial solutions can be clarified by filtering before drying by spray drying. Off-yellowing solids were obtained after the drying process which can be redissolved showing the same translucency/transparency as the corresponding initial solutions (before drying).

Example 1

Preparation of a MMST Formulation with Arabic Gum

Commercially available potassium methyl siliconate ($CH_3K_3O_3Si$) was used as silicon source.
A) Preparation of a MMST Solution (10 g Si/L)
In a round-bottomed flask equipped with magnetic stirrer, deionized water (350 mL), $H_3PO_4$ (4 grams) and $CH_3K_3O_3Si$ (40 grams) were combined and stirred at RT overnight. The resulting solution was diluted to 500 mL with deionized water (final pH 2.9).
B) Preparation of Microparticles of MMST and Gum Arabic
In a round-bottomed flask equipped with magnetic stirrer, arabic gum (128 g) was added to deionized water (500 mL) under stirring at RT for 1 h. Then, the MMST solution (200 mL, 10 g Si/L) prepared in section A) was added and the mixture was stirred at RT for 10 min. The obtained brownish translucent solution was filtered with a filter paper and dried by spray drying giving an off-yellowing solid (85.7 g, approx. 63% yield). The obtained powder was diluted to 1 L (solution 10 g Si/L) with deionized water (the solution had a pH of 10).
C) Stability of the Obtained Solid Formulation
The stability of four solid formulation obtained as mentioned above was checked periodically by dissolving a solid sample in water in order to obtain a solution with approximately 1 g Si/L (ca. 0.3 g of solid in 4 mL of water). Non-stable solid formulations are expected to give solutions having a solid residue.

After 3 months the four solid formulations were stable: when re-dissolving the obtained solid formulation, a solution with the same transparency/translucency than the ones obtained with the freshly prepared solid formulation was obtained after 3 months.
D) Analysis of the Amount of MMST in the Microparticles
The concentration of MMST in the solid obtained above was determined by $^1$H-NMR with presaturation.

Preparation of the test sample: 50.7 mg of sample were weighed and dissolved in 1 ml of $D_2O$ (99.8% D). 20 µL of sodium trimethylsilylpropionate (TSP) standard solution (20 mg TSP/5 mL $D_2O$) were added to quantify and reference (signal at 0 ppm).

The identification of the product was carried out by using a NMR spectrometer equipped with a Prodigy cryoprobe. As a standard MMST dissolved in $H_2O$ at a pH 3,5 was used.

Figure 3:
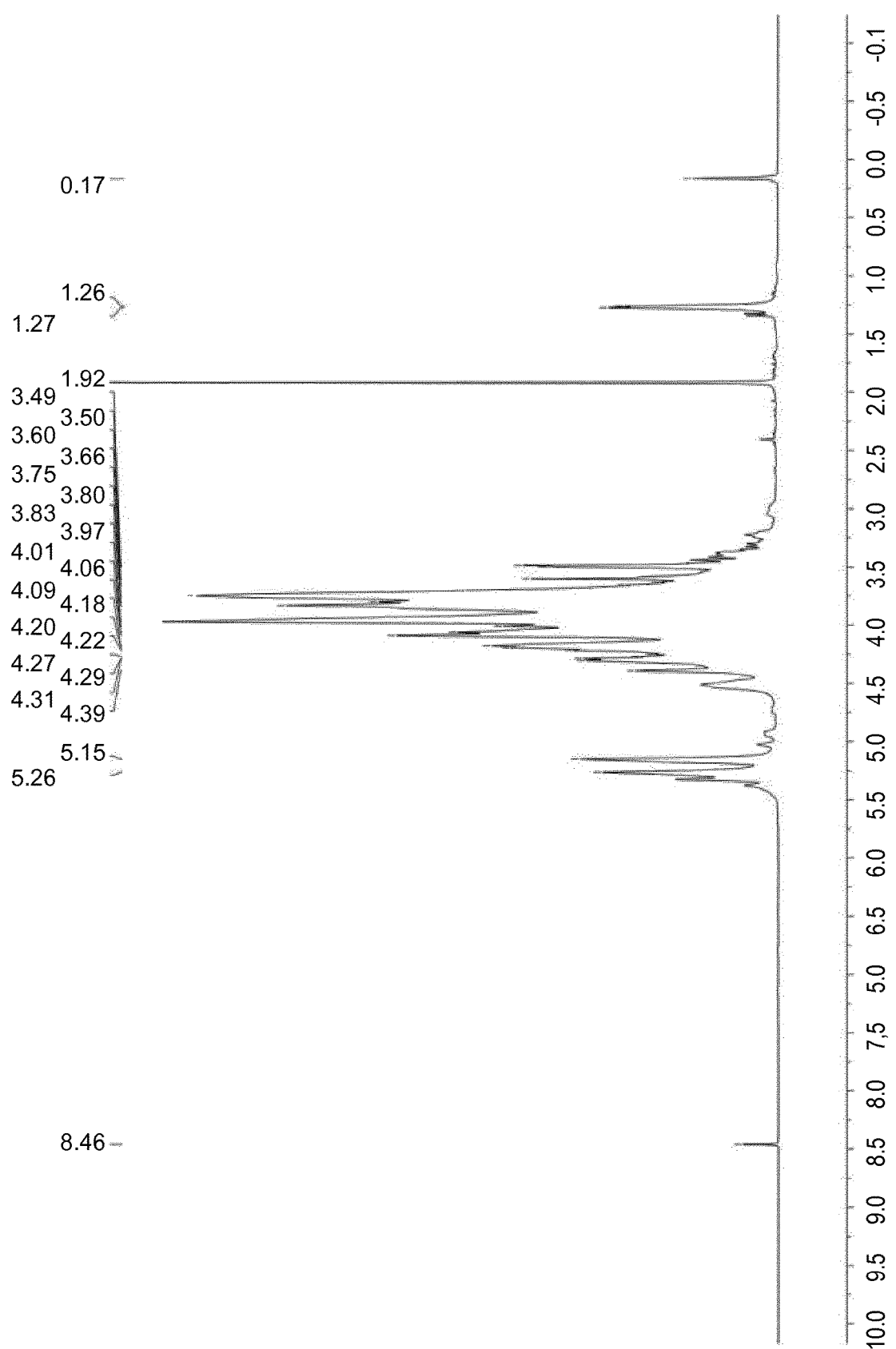
FIG. 3 shows the $^1$H-NMR spectrum of the sample of microparticles of MMST and gum arabic obtained in Example 1.
Figure 4:
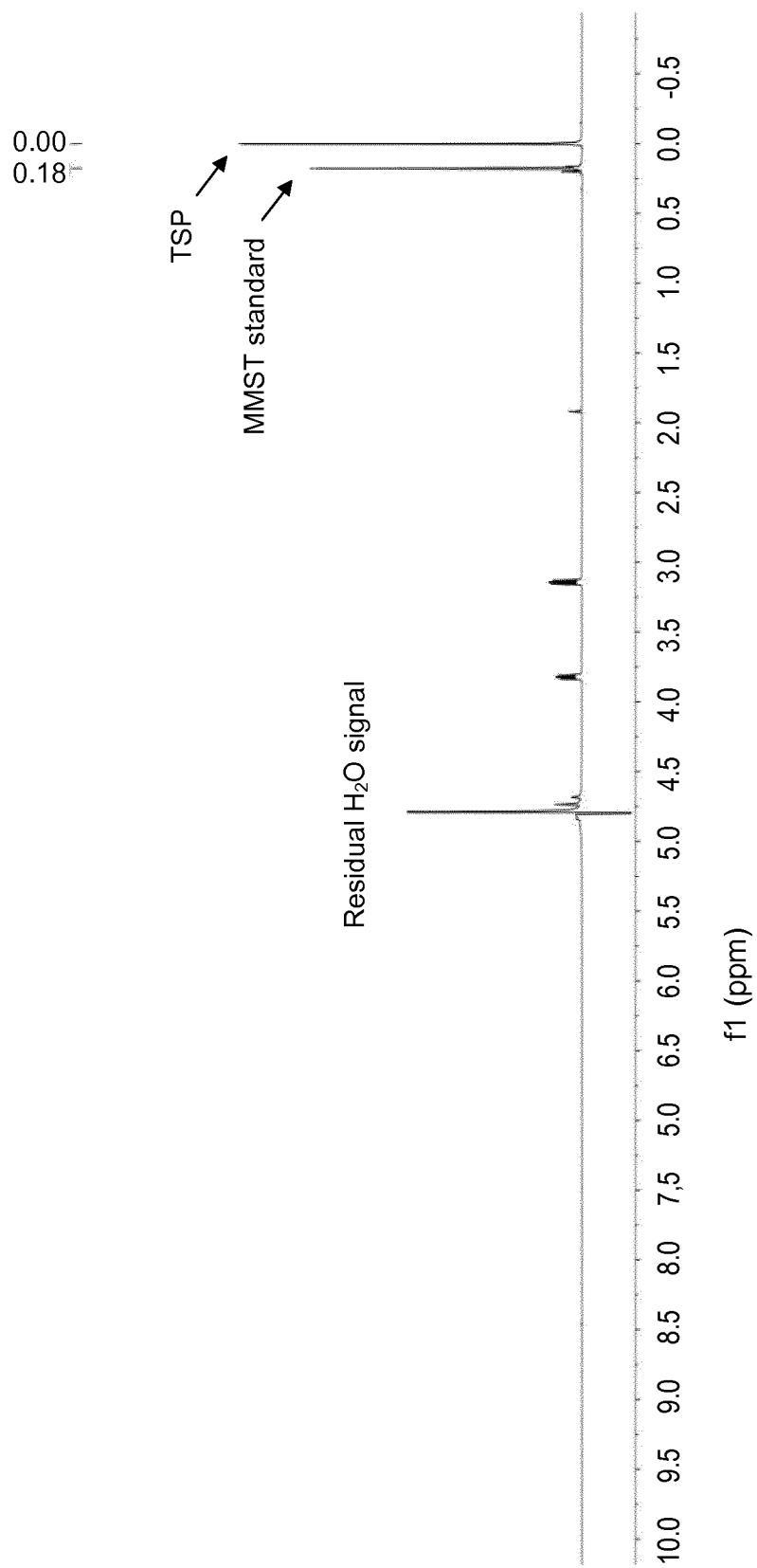
FIG. 4 shows the $^1$H-NMR spectrum of the MMST pattern.
Figure 5:
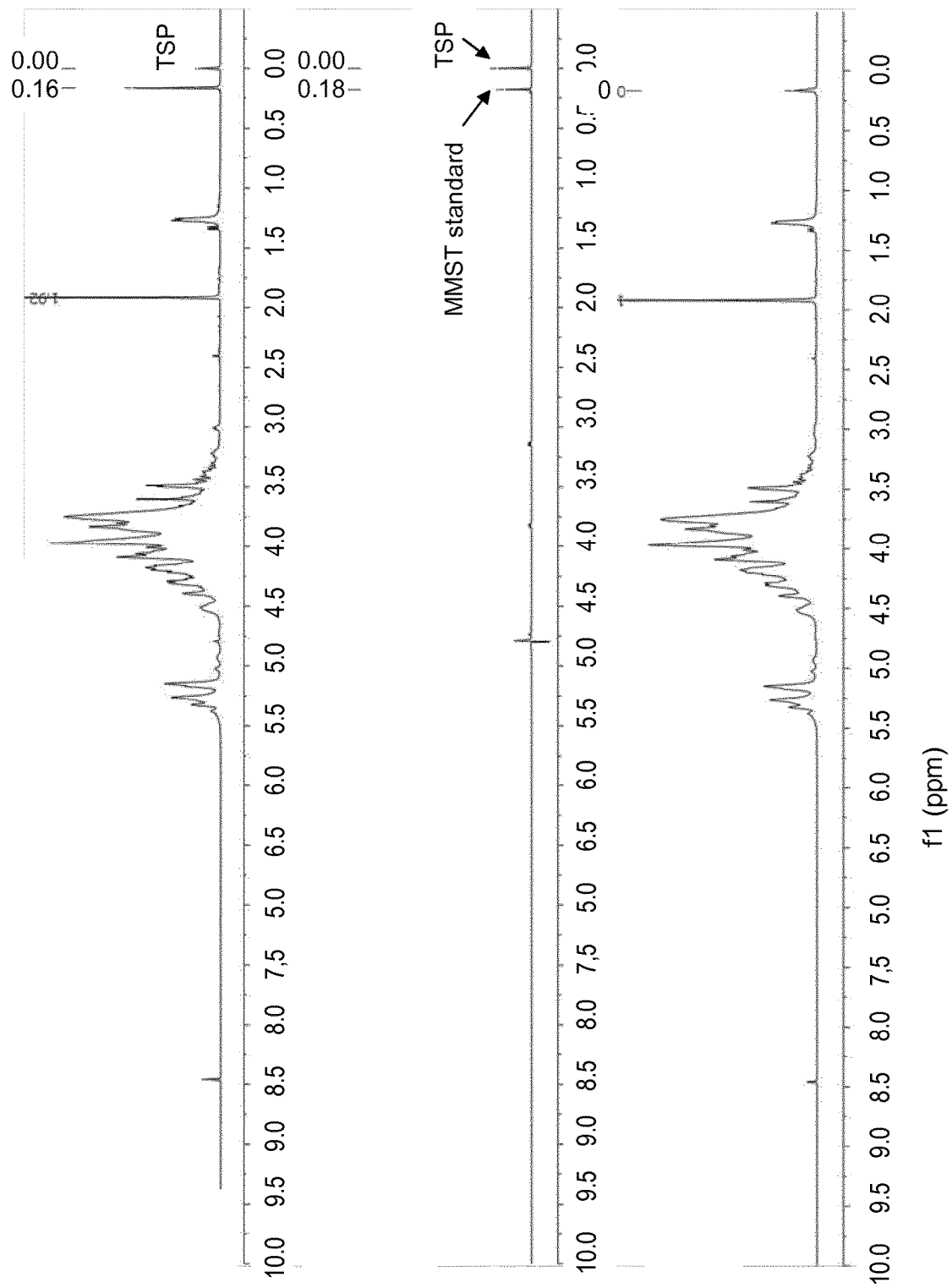
FIG. 5 shows the comparison of the problem sample (below), MMST standard+TSP (medium) and mixture of both (above). It is observed that when the MMST standard is added to the dissolved sample of MMST-gum arabic the MMST signal increases.

Firstly, a $^1$H-NMR of the sample dissolved in $D_2O$ (see FIG. 3) was obtained. A signal at 0.17 ppm compatible with the MMST methyl proton was observed. Measurement was carried out at 25° C. Then, a sample was prepared with the pure MMST standard dissolved in $D_2O$. TSP was added for reference, signal at 0 ppm (see FIG. 4). Finally, 350 µl of the solution prepared from the test sample were mixed with 350 µl of the MMST standard, respectively (FIG. 5).

Once the product was identified, a $^1$H-NMR spectrum of the sample MMST-gum arabic (FIGS. 6 and 7) was performed to quantify the % of MMST present. For this, 20 µL of a TSP standard solution (20 mg TSP/5 mL $D_2O$) was added to the sample. From the integration data of the signals involved, it was determined that sample of MMST-gum arabic contained a 1.16 wt % of monomeric MMST.

Example 2

Preparation of an Orthosilicic Acid (OSA) Formulation with Arabic Gum

Tetraethyl orthosilicate ($Si(OC_2H_5)_4$: TEOS; was used as silicon source.
A) Preparation of an OSA Solution (10 g Si/L)
In a round-bottomed flask equipped with magnetic stirrer, deionized water (330 mL), $H_3PO_4$ (1.17 grams) and TEOS (38 grams) were combined and stirred at RT overnight. The resulting solution was diluted to 500 mL with deionized water (final pH 2.2). The hydrolysis of TEOS was allowed to evolve overnight and then it was confirmed by GC (gas chromatography) that no unreacted TEOS remained in the final solution.
B) Preparation of Microparticles of OSA and Gum Arabic
In a round-bottomed flask equipped with magnetic stirrer, arabic gum (128 g) was added to deionized water (500 mL) under stirring at RT for 1 h. Then, the MMST solution (200 mL, 10 g Si/L) was added and it was stirred at RT for 10 min. The obtained brownish translucent solution was diluted to 1

L with deionized water (measured pH 4.5), filtered with a filter paper and dried by spray drying giving an off-white solid (85.7 g, approx. 63% yield).

C) Stability of the Obtained Solid Formulation

The stability of four solid formulation obtained as mentioned above was checked periodically by dissolving a solid sample in water in order to obtain a solution with approximately 1 g Si/L (ca. 0.3 g of solid in 4 mL of water). Non-stable solid formulations are expected to give solutions having a solid residue.

After 3 months the four solid formulations were stable: when redissolving the obtained solid formulation, a solution with the same transparency/translucency than the ones obtained with the freshly prepared solid formulation was obtained after 3 months.

Example 3

Preparation of a MMST Solution from Methyltriethoxysilane (MTES)

In a round-bottomed flask equipped with magnetic stirrer, water (100 mL), citric acid monohydrate (11.2 mg) and MTES (76.3 mg) were combined and stirred at RT overnight. Potassium sorbate (50 mg) and sodium benzoate (25 mg) were added, the pH was adjusted with 1M HCl aq (pH=3.64) and the resulting solution was filtered with a Whatman glass microfiber filter (GF/C) and contained 0.1 g Si/L.

This MMST solution obtained from MTES, which is somehow more stable than the one obtained in Example 1, A) from $CH_3K_3O_3Si$, can be used for the preparation of microparticles of MMST and gum arabic analogously as disclosed in section B) of Example 1.

The invention claimed is:

1. A combination of an organosilicon compound and arabic gum in the form of microparticles, wherein
   the organosilicon compound has the formula (I):

$$R^4-Si(OR^1)(OR^2)R^3,\qquad(I)$$

wherein $R^1$ and $R^2$ are independently selected from hydrogen and a ($C_1$-$C_4$)alkyl group; $R^3$ is hydroxyl; and $R^4$ is hydroxyl or a ($C_1$-$C_4$)alkyl group;
   wherein the arabic gum forms a polymeric matrix having interspaces, and
   wherein the organosilicon compound is distributed in the interspaces of the polymeric matrix.

2. The combination according to claim 1, wherein $R^4$ is a ($C_1$-$C_4$)alkyl group.

3. The combination according to claim 2, wherein $R^4$ is methyl.

4. The combination according to claim 1, wherein the organosilicon compound is monomethylsilanetriol.

5. The combination according to claim 1, wherein the organosilicon compound is orthosilicic acid.

6. The combination according to claim 1, wherein microparticles have a diameter selected from 10 to 250 µm.

7. The combination according to claim 1, wherein the organosilicon compound is in an amount selected from 1 to 10 wt % relative to the total weight of the composition.

8. A process for the preparation of the combination in solid form as defined in claim 1 comprising:
   a) preparing an aqueous solution of the organosilicon compound of formula (I) as defined in claim 1;
   b) mixing the solution with a suitable amount of arabic gum in order to obtain an aqueous suspension; and
   c) drying the suspension by spray drying in order to obtain a solid product.

9. The process according to claim 8, wherein spray drying is carried out in a spray dryer equipped with a nozzle of a diameter selected from 1 to 40 mm.

10. The process according to claim 9, wherein spray drying is carried out at a rotational speed selected from 17000 to 19000 rpm.

11. The process according to claim 10, wherein spray drying is carried out in a spray dryer with an inlet temperature selected from 210 to 230° C. and an outlet temperature from 90 to 120° C.

12. The process according to claim 8, wherein the organosilicon compound is monomethylsilanetriol.

13. The process according to claim 12, further comprising before step a), a step of hydrolyzing methyltriethyoxysilane with a weak acid in order to obtain the aqueous solution of monomethylsilanetriol.

14. A dietary supplement comprising the combination of an organosilicon compound and arabic gum in the form of microparticles as defined in claim 1.

15. A pharmaceutical or a cosmetic composition comprising the combination of an organosilicon compound and arabic gum in the form of microparticles as defined in claim 1, together with pharmaceutically or cosmetically acceptable excipients or carriers.

16. The process according to claim 8, wherein the organosilicon compound is orthosilicic acid.

17. The dietary supplement as defined in claim 14, wherein the organosilicon compound is monomethylsilanetriol.

18. The dietary supplement as defined in claim 14, wherein the organosilicon compound is orthosilicic acid.

19. The pharmaceutical or cosmetic composition of claim 15, wherein the organosilicon compound is monomethylsilanetriol.

20. The pharmaceutical or cosmetic composition of claim 15, wherein the organosilicon compound is orthosilicic acid.

* * * * *